United States Patent
Myklebust

(10) Patent No.: US 8,672,867 B2
(45) Date of Patent: Mar. 18, 2014

(54) CARDIOPULMONARY BYPASS DEVICES AND METHODS

(75) Inventor: Helge Myklebust, Stavanger (NO)

(73) Assignee: Laerdal Medical AS, Stavanger (NO)

( * ) Notice: Subject to any disclaimer, the term of this patent is extended or adjusted under 35 U.S.C. 154(b) by 973 days.

(21) Appl. No.: 12/123,967

(22) Filed: May 20, 2008

(65) Prior Publication Data

US 2008/0294252 A1 Nov. 27, 2008

(30) Foreign Application Priority Data

May 23, 2007 (GB) .................................. 0709908.8

(51) Int. Cl.
*A61M 1/36* (2006.01)

(52) U.S. Cl.
USPC .................... 604/4.01; 604/6.14; 604/6.13

(58) Field of Classification Search
USPC ................ 600/16; 623/3.1; 604/4.01, 7, 6.14
See application file for complete search history.

(56) References Cited

U.S. PATENT DOCUMENTS

| | | | |
|---|---|---|---|
| 3,513,845 A * | 5/1970 | Callaghan et al. ............. 604/6.1 |
| 4,756,705 A | 7/1988 | Beijbom et al. ................... 604/4 |
| 5,158,534 A * | 10/1992 | Berry et al. ................... 604/6.14 |
| 5,308,320 A | 5/1994 | Safar et al. ......................... 604/4 |
| 5,403,281 A * | 4/1995 | O'Neill et al. ................. 604/113 |
| 5,423,749 A * | 6/1995 | Merte et al. ...................... 604/67 |
| 5,466,216 A | 11/1995 | Brown et al. ..................... 604/33 |
| 5,584,804 A * | 12/1996 | Klatz et al. ....................... 604/24 |
| 6,024,692 A * | 2/2000 | Dilling ............................ 600/17 |
| 6,241,699 B1 | 6/2001 | Suresh et al. |
| 6,702,773 B1 * | 3/2004 | Macoviak et al. ............ 604/4.01 |
| 6,983,749 B2 * | 1/2006 | Kumar et al. ............. 128/204.15 |
| 7,381,179 B2 * | 6/2008 | Aboul-Hosn et al. ........... 600/16 |
| 7,435,220 B2 * | 10/2008 | Ranucci ......................... 600/483 |
| 7,588,549 B2 * | 9/2009 | Eccleston .................... 604/4.01 |
| 2002/0161322 A1 * | 10/2002 | Utterberg et al. ............. 604/6.16 |
| 2003/0044315 A1 * | 3/2003 | Boekstegers ..................... 422/44 |
| 2003/0194348 A1 * | 10/2003 | Divino et al. .................... 422/45 |
| 2004/0064091 A1 * | 4/2004 | Keren et al. ................. 604/96.01 |
| 2004/0138608 A1 * | 7/2004 | Barbut et al. ................. 604/6.13 |
| 2005/0027231 A1 | 2/2005 | Kirchhof ...................... 604/4.01 |

(Continued)

FOREIGN PATENT DOCUMENTS

| | | |
|---|---|---|
| EP | 1 457 218 A1 | 9/2004 |
| WO | WO 90/15631 | 12/1990 |
| WO | 2005/046779 A2 | 5/2005 |
| WO | WO 2006/039218 A2 | 4/2006 |

OTHER PUBLICATIONS

Vanden Hoek et al., "Reperfusion, not simulated ischemia, initiates intrinsic apoptosis injury in chick cardiomyocytes", Am J. Physiol Heart Circ Physiol; 284:H141-H150, 2003.

(Continued)

*Primary Examiner* — Susan Su
(74) *Attorney, Agent, or Firm* — Dorsey & Whitney LLP

(57) ABSTRACT

A cardiopulmonary bypass device may include a first tube configured for connection to a vein and a second tube configured for connection to an artery. The device may further include a pump connected between the first and second tubes. In a first mode, the pump may pump fluid in one direction and in a second mode, the pump may pump fluid in the opposite direction. A control unit may be coupled to the pump to control its operation. Lungs may functions as the oxygenator of the cardiopulmonary bypass device.

27 Claims, 2 Drawing Sheets

(56) References Cited

U.S. PATENT DOCUMENTS

| | | | |
|---|---|---|---|
| 2005/0082226 A1* | 4/2005 | Bene et al. | 210/646 |
| 2005/0084416 A1* | 4/2005 | Thomas | 422/45 |
| 2005/0234288 A1* | 10/2005 | Aboul-Hosn et al. | 600/16 |
| 2006/0041217 A1* | 2/2006 | Halperin et al. | 604/6.13 |
| 2006/0052715 A1* | 3/2006 | Krivitski | 600/508 |
| 2006/0100565 A1* | 5/2006 | Aboul-Hosn | 604/9 |
| 2006/0100639 A1* | 5/2006 | Levin et al. | 606/106 |
| 2006/0173396 A1* | 8/2006 | Hatamian et al. | 604/6.13 |
| 2006/0257283 A1 | 11/2006 | Ranucci | |
| 2006/0258981 A1* | 11/2006 | Eidenschink | 604/103.1 |
| 2006/0281962 A1* | 12/2006 | Bolling et al. | 600/16 |
| 2010/0076095 A1* | 3/2010 | Thomas et al. | 514/789 |

OTHER PUBLICATIONS

Abella et al., "Intra-Arrest Cooling Improves Outcomes in a Murine Cardiac Arrest Model.", Circulation Journal of the American Heart Association, vol. 109, No. 22, Jun. 8, 2004; pp. 2786-2791.

Search report issued on Feb. 4, 2011 in French application No. 0853373.

* cited by examiner

CARDIOPULMONARY BYPASS DEVICES AND METHODS

CROSS-REFERENCE TO RELATED APPLICATION(S)

This application claims the benefit of United Kingdom Application No. 0709908.8, entitled "CARDIOPULMONARY BYPASS DEVICE", filed May 23, 2007, which application is hereby incorporated by reference in its entirety.

TECHNICAL FIELD

This invention relates to cardiopulmonary bypass devices and methods.

BACKGROUND OF THE INVENTION

Despite investments in research, in training, in equipment and infrastructure, survival from unexpected cardiac arrest has been virtually unchanged over the past couple of decades. On average, the survival rate is approximately 5% in USA/Europe, but can even be as low as 2% in the bigger cities, or well above 20% in those cities with the best implementation of science and education.

One factor influencing survival is time elapsed from cardiac arrest onset until professional treatment begins. This time varies a lot. It is known that the vital organs can sustain approximately 5-10 minutes without perfusion before resuscitation becomes effective, and after that time the chance of survival is reduced by about 5-10% for every minute, so that after about 15 to 20 minutes survival chances are very small.

There is thus a need for expanding the time window of opportunity of recovering from cardiac arrest.

One other factor of survival is that current treatment of chest compressions, ventilations, defibrillation and drugs does not address the underlying cause of the arrest. Some hearts are simply too compromised to be restarted, even though CPR, drugs and defibrillation are delivered according to best practice. Many patients who do not receive return of spontaneous circulation within some minutes of resuscitation attempts could benefit from receiving continuous CPR to keep vital organs intact, followed by application of some external means of circulation to buy enough time so that corrective treatment can be done in the hospital.

Another factor affecting survival is reperfusion injury. Cell death does not only take place as a result of ischemia, but also as a function of reperfusion. Given the situation of sudden cardiac arrest, most of the cell death and subsequent irreversible organ damage may take place when perfusion is restored because of the circulation of toxic components that have built up during ischemia. This is described for example by Vanden Hoek, et. al. "Reperfusion, not simulated ischemia, initiates intrinsic apoptosis injury in chick cardiomyocytes", Am J Physiol Heart Circ Physiol, 284:H141-H150, 2003.

One factor that can improve survival is induced hypothermia. Therapeutic hypothermia can be beneficial after cardiac arrest, and intra-arrest cooling can be beneficial with both respect to defibrillation success and survival to discharge from hospital. Cooling also seems to slow down the speed of cell death caused by reperfusion after cardiac arrest. This is for example described by Abella, et al. in "Intra-Arrest Cooling Improves Outcomes in a Murine Cardiac Arrest Model.", Circulation 2004; 109; 2786-2791.

The most used way to increase the time window is to perform cardiopulmonary resuscitation (CPR) on the victim of cardiac arrest. CPR is a procedure performed as life-saving first aid in case of a sudden cardiac arrest. The procedure comprises chest compressions and ventilation. There are, however, limits to this method. The person performing CPR may not be sufficiently skilled or motivated, there are difficulties performing CPR in an ambulance, there may not be enough rescuers available to perform CPR while performing other necessary activities at the same time, it is difficult to perform CPR over a long period of time, and the effectiveness of CPR to generate flow is also reduced by time.

This has led to a need for emergency cardiopulmonary bypass (eCPB). Cardiopulmonary bypass (CPB) (also sometimes referred to as heart-lung machine) is a technique that temporarily takes over the function of the heart and lungs during cardiac arrest. This has traditionally been used in hospitals during surgery, for induction of total body hypothermia, as life support for newborns with serious birth defects, or to oxygenate and maintain recipients for organ transplantation until new organs can be found. Such traditional machines are typically not suited for emergency use, as they are not portable, they require particular skills to operate and are not easily transported to the location where a cardiac arrest or trauma victim is located. But there is now a growing application of CPB even for cardiac arrest patients.

U.S. Pat. No. 5,308,320 describes a portable and modular cardiopulmonary bypass apparatus that can be transported to an accident scene or heart attack victim. The apparatus comprises balloon catheters which are used to distribute the blood flow to specific parts of the body, for example to administer medication only to some parts of the body.

US Published Application 2005/0027231 describes a mobile heart-lung machine which comprises two separate modules. One module comprises elements which circulate the blood, receive the biochemical and physiological signals and implement the control signals, this is a so-called "disposable module". The other module comprises drive and automatic control elements, a so-called "reusable module". This two-module design enables quick re-use of the machine.

These cardiopulmonary bypass apparatuses have an oxygenator in the bypass circuit which transfers oxygen to infused blood and removes carbon dioxide from the venous blood, that is, gas exchange occurs. The oxygenator is a risk factor of these apparatuses, as the blood is exposed to a huge surface area of the oxygenator and may coagulate. The oxygenator is also large and makes the apparatus large and complex and more costly in use.

U.S. Pat. No. 4,756,705 describes a heart-lung system that uses the patient's lungs as an oxygenator. The heart and lungs are coupled in two circuits, collecting blood from the heart in a venous reservoir, sending it through the lungs, and collecting the oxygenated blood in an arterial reservoir where it is warmed and sent into the body.

This is a complicated system with a plurality of catheters, two separate pumps for pumping the blood into the body and two separate blood reservoirs. This system will not be suited for emergency use and is not portable.

DETAILED DESCRIPTION

Certain details are set forth below to provide a sufficient understanding of embodiments of the invention. However, it will be clear to one skilled in the art that embodiments of the invention may be practiced without various of these particular details. In some instances, well-known circuits, control signals, timing protocols, and software operations have not been shown in detail in order to avoid unnecessarily obscuring the described embodiments of the invention. The invention is not limited to an emergency cardiopulmonary bypass apparatus, the apparatus according to the invention may also be used in hospitals for more traditional operations which require use of cardiopulmonary bypass.

Figure 1:
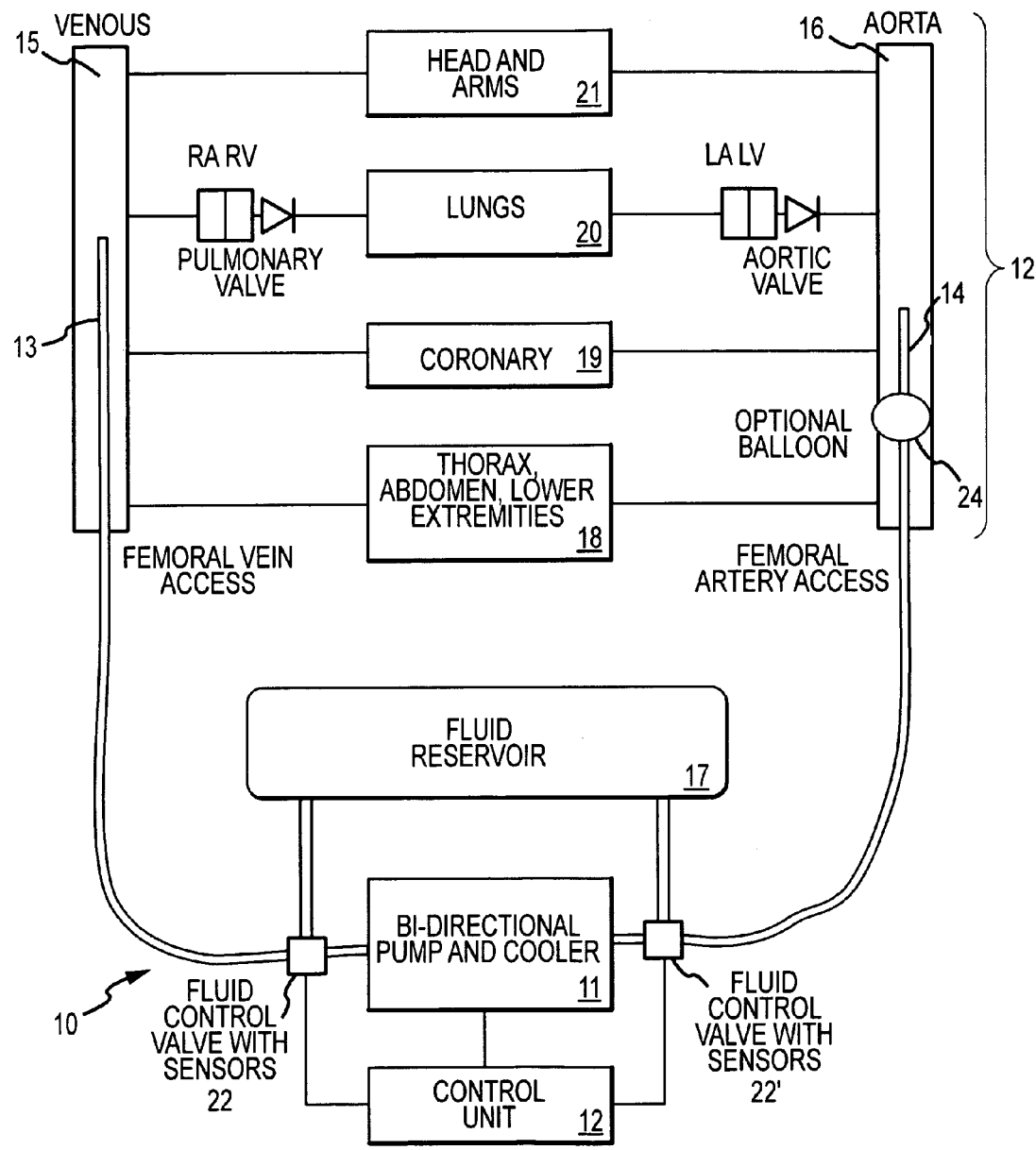
FIG. 1 is a block diagram schematically depicting a model of a cardiopulmonary bypass device according to an embodiment of the present invention connected to a body.

FIG. 1 illustrates a block diagram of a cardiopulmonary bypass device 10 according to an embodiment of the present invention connected to a body. The device 10 includes first 13 and second 14 tubes for connection to veins 15 and arteries 16, respectively. Elements 15 and 16 may represent a main vein and artery, for example the femoral vein and artery, although other veins and arteries may be used. Generally, the first tube 13 is configured for connection to a vein and the second tube 14 is configure for connection to an artery. The first and second tubes 13, 14 may be implemented using cannulas, catheters or other tubular devices that are suited for withdrawing and/or returning blood from/to veins/arteries.

Connected between the first 13 and second 14 tubes is a pump 11, in the example of FIG. 1, a bi-directional pump, connected to a cooler. The cooler can cool the blood in order to reduce the level of metabolism and thus increase chances of recovery. The pump 11 may be any suitable pump. A roller pump may be a suitable choice from the point of view of cost, complexity and risk. A roller pump generally has no contact with the pumped fluid, but moves the fluid inside a tubing by pushing a set of rollers against the tubing in the desired direction of the flow. The pump 11 may be a bi-directional pump, as shown in FIG. 1, or may be connected to an arrangement, for example of valves, which enables pumping in two different directions.

The pump 11 is connected between the first and second tubes 13, 14 and configured in a first mode to pump fluid in one direction and in a second mode to pump fluid in the opposite direction. A control unit 12 is connected to the pump and controls the pump with respect to flow volume, flow direction, flow rate, etc. The control unit 12 may also control other controllable units that may be coupled to it. The control unit 12 may be implemented using a mechanical device, an electrical device, or a combination of electrical and mechanical devices, which can set the direction and/or magnitude of the flow out of the pump. A mechanical control unit for a motor, for example, may be implemented as a coupling between motor and rotor configured to change the rotation direction after a certain number of rotations, or the like. An electrical control unit may for example include a programmable logic controller or another programmable device which is connected to the motor.

Referring again to FIG. 1, a set of sensors 22 and 22' is connected to control unit 12 and may be used as input for controlling the pump 11. The sensors might be arranged to measure time, temperature, oxygenation (e.g. by infrared spectroscopy), blood gases, pressure, flow, carbon dioxide, etc. The sensor signals may be used by the control unit 12, for example, the control unit 12 may compare measurement data from the sensors 22 and 22' with threshold levels or acceptable ranges, and generate a control signal based on the comparison.

When the device 10 is operating in a first, forward mode, blood is drained from the vein 16 and pumped into the artery 15. This results in a perfusion pressure which drives blood through the head and arms 21, the heart 19 and the lower portions 18 of the body. During this forward mode, oxygen is consumed, leading to a change in the $O_2$ or $CO_2$ levels.

In one embodiment, the control unit 12 may operate the pump 11 in forward mode until the sensors 22 or 22' indicate that the level of $O_2$ or $CO_2$ is outside a desired range, for example below a preset lower or upper level respectively. When this happens, the control unit 12 may reverse the pump 11, pumping blood through the lungs 20, where gas exchange takes place, until the sensors 22 or 22' indicate that a desired set level has been reached. This may require some method of activating lung ventilation.

In one embodiment, the control unit 12 may emit a signal to an operator (not shown) to begin ventilation, for example by using a manual resuscitator. In another embodiment, the control unit 12 may send a signal to an automatic ventilator, to start ventilating. In another embodiment, a Continuous Insufflation of Oxygen (CIO) tube is provided such that there is a continuous flow of oxygen into the lungs (for example, 15-30 liters per minute may be sufficient) which causes gas exchange and some level of CPAP (continuous positive airway pressure) to help keep the lungs dilated to ensure effective lung area for gas exchange. Combinations of these ventilation methods, or other ventilation methods, may also be used. The control unit 12 may use data from sensors 22, 22' or both, in order to control the ventilation device, for example oxygen and $CO_2$ sensor signals indicating the need for more or less oxygen in the blood may be used for controlling the ventilation rate or volume.

In embodiments of the present invention, the pump 11 provides circulation in the forward direction for a preset time, such as a preset number of seconds, followed by a second preset time period with circulation in the reverse direction, and so on. Some method of signalling might be provided to the operator to understand when the pump is operating in the reverse direction, such that the operator can deliver ventilations at the same time. Such signalling means may produce visual or audible feedback signals, or a combination thereof. The control unit 12, for example, may include a feedback device for giving feedback to a rescuer. The feedback may for example include instructions on how to improve the ventilations by increasing/decreasing ventilation rate and/or volume.

Also shown in FIG. 1 is an inflatable/deflatable balloon 24 arranged in the second tube 16. The balloon 24 is situated such that when inflated, it prevents some of the blood from going to the lower regions of the body. This inflation/deflation of the balloon prevents/allows blood flow, for example preventing/lowering the blood flow to the lower parts of the body where the blood flow is less critical, thus allowing more blood flow to head and heart. Inflation of the balloon 24 can be either manual or automated. If automated, its inflation and deflation may be controlled from the control unit 12.

While a balloon 24 is shown in FIG. 1, other variable restrictions may be connected to the second tube 16 in other embodiments. The restriction may be arranged in or adjacent to the tube in a position where the degree of restriction directs the blood flow to specific parts of the body.

In cardiac arrest and during periods of low flow, the level of metabolism is reduced compared to normal. With temperature reduction, which takes place spontaneously during cardiac arrest and shock, and which can be further achieved by applying cooling techniques, the level of metabolism is even further reduced. Pump 11 can thus in some cases be designed to deliver less than normal levels of circulation without this having a detrimental effect. This will allow miniaturization and a lower cost of the pump assembly.

In order to prevent or slow down the speed of cell death associated with reperfusion, the pump 11 may be arranged in combination with a heat exchange mechanism, to allow rapid cooling of the blood. This is typically done by allowing the tubes carrying blood to be submerged in a cooled fluid, where the tube material is such that heat transfer is sufficiently effective.

Because the vessels in the body tend to lose tone in cardiac arrest, the vessels may dilate. This may have two effects: firstly, the effective blood volume needed to fill the vessels increases, and secondly, the vascular resistance decreases. In order to compensate for the relative loss in effective vascular volume, the device 10 according to an embodiment of the invention may include a fluid reservoir 17 connected to the low pressure side of the pump 11. As the low pressure side will alternate when the pump direction alternates, the fluid reservoir may be connected to both sides of the pump, as shown in FIG. 1, and the connections to the reservoir 17 opened and closed as the pumping direction changes. This opening/closing of the connections may be arranged by the provision of one one-way valve in each connection, or by electromagnetically controlled valves connected to and controlled by the control unit 12. In operation, if the amount of blood that can be drained from the low pressure side is less than what is needed to generate a desired perfusion pressure, the control unit 12 may open up for fluid supply from the fluid reservoir 17.

The fluid reservoir 17 might also provide for drug delivery, as some drugs have proven effective to reduce the speed of cell death caused by reperfusion. Accordingly, the fluid reservoir 17 can contain blood, saline, drugs, blood components, etc. The fluid reservoir may also be cooled.

Accordingly, the cardiopulmonary bypass device 10 according to an embodiment of the invention does not require an external oxygenator.

Figure 2:
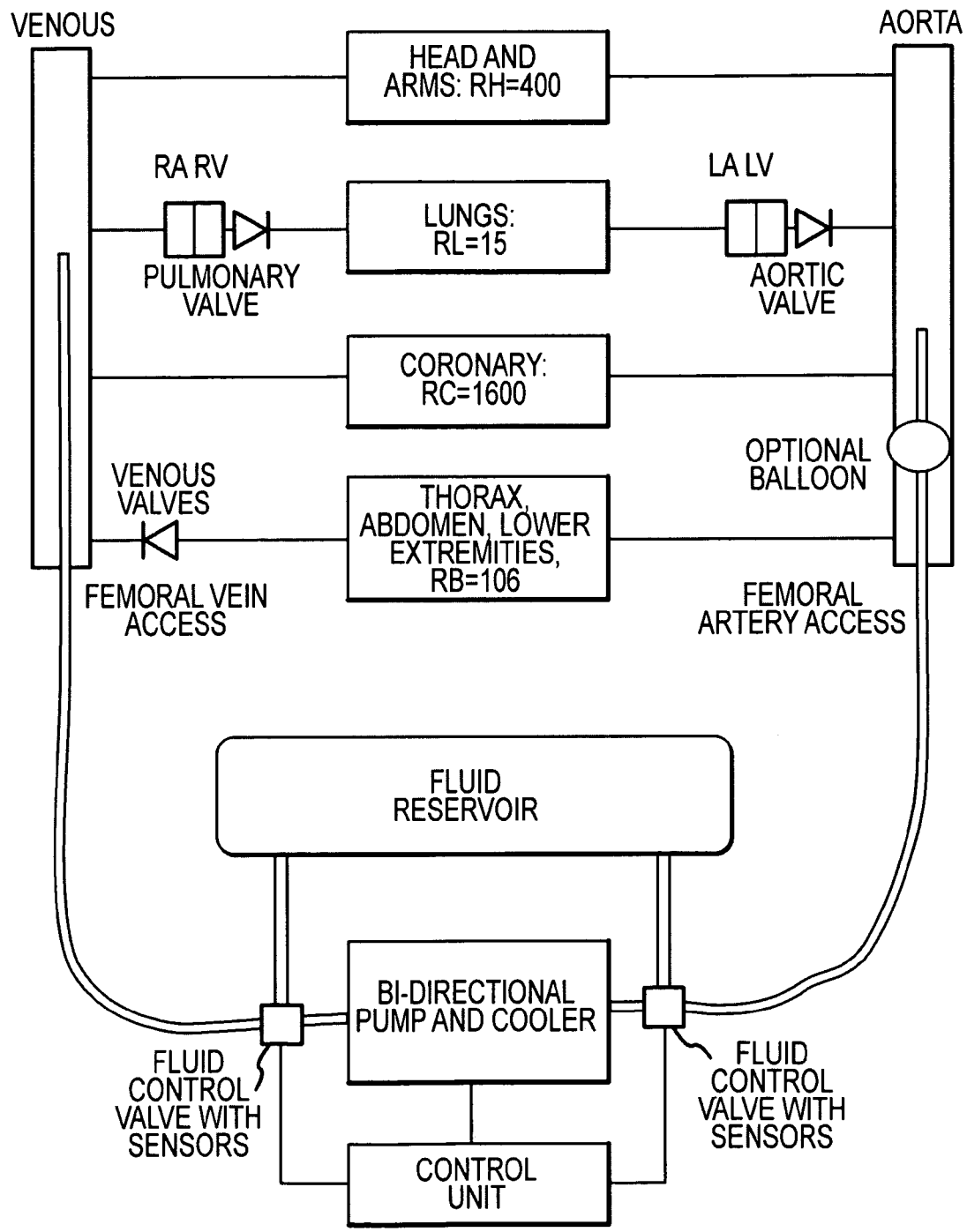
FIG. 2 is a block diagram depicting a model of a cardiopulmonary bypass device that includes vascular resistance of different parts of a body according to an embodiment of the present invention.

In FIG. 2, typical units of vascular resistance are shown for each of the different portions of the body. The vascular resistance values are shown to aid in a description of an embodiment of the invention, and the values are not intended to limit the invention or restrict use of the invention to bodies having the values shown.

Typically, the blood circulates at 5 l/min. By normalizing this flow to 1, and by considering a typical distribution of flow, it can be calculated that:

| | |
|---|---|
| Flow to head and arms | 20% |
| Average perfusion pressure | 80 mmHg |
| Vascular resistance | 80/0.2 = 400 |
| Flow to coronary | 5% |
| Average perfusion pressure | 80 mmHg |
| Vascular resistance | 80/0.05 = 1600 |
| Flow to lower body | 75% |
| Average perfusion pressure | 80 mmHg |
| Vascular resistance | 80/0.75 = 106 |
| Flow trough lungs | 100% |
| Average perfusion pressure | 15 mmHg |
| Vascular resistance | 15/1 = 15 |

These numbers indicate a balloon may be effective in directing the forward flow to heart and brain.

These numbers also indicate that only a small pressure may be needed in the venous side in order to have a perfusion pressure over the lungs sufficient to cause blood flow necessary for effective gas exchange. For instance, if the pump could deliver 5 l/min, it would just take about one minute to circulate the full systemic volume through the lungs, and with a perfusion pressure of 15 mmHg it is likely that the venous pressure will be close to 20 mmHg, which might not be a problem.

It is further assumed in the model in FIG. 2 that the pulmonary valve and the aortic valve are functional, such that pulmonary retrograde flow is limited. The model also includes the venous valves in the lower body. These are not essential, because the vascular resistance is so much lower in the lungs, and any retrograde flow in the lower body may cause little reduction in pulmonary antegrade flow.

In the figures:
RA denotes Right Atrium
RV denotes Right Ventricle
LA denotes Left Atrium
LV denotes Left Ventricle From the foregoing it will be appreciated that, although specific embodiments of the invention have been described herein for purposes of illustration, various modifications may be made without deviating from the spirit and scope of the invention.

What is claimed is:

1. A cardiopulmonary bypass device comprising:
   a first tube configured to connect with at least one vein;
   a second tube configured to connect with at least one artery;
   a pump connected between the first and second tubes and configured to pump fluid in a first direction in a first mode and to pump fluid in a second direction, opposite to the first direction, in a second mode;
   a heat exchange mechanism connected to the pump and configured to cool a fluid; and
   a control unit connected to the pump and configured to control operation of the pump, the control unit further configured to send a signal to activate lung ventilation.

2. The cardiopulmonary bypass device according to claim 1 wherein the first direction is from the at least one vein to the at least one artery and the second direction is from the at least one artery to the at least one vein.

3. The cardiopulmonary bypass device according to claim 2 wherein the fluid includes blood and the pump operating in the first mode is configured to drive the blood through at least a heart of a body connected to the cardiopulmonary bypass device.

4. The cardiopulmonary bypass device according to claim 3 wherein the pump operating in the second mode is configured to drive the blood through lungs of the body connected to the cardiopulmonary device.

5. The cardiopulmonary bypass device according to claim 1, wherein the pump includes a roller pump.

6. The cardiopulmonary bypass device according to claim 1, further comprising a fluid reservoir connected to the pump.

7. The cardiopulmonary device according to claim 6, wherein the fluid reservoir is connected to the pump and configured to transfer fluid to a first side of the pump having a lower pressure than a second side of the pump.

8. The cardiopulmonary device according to claim 7, wherein the fluid reservoir is connected to both sides of the pump.

9. The cardiopulmonary device according to claim 8, wherein the fluid reservoir comprises:
   a first one-way valve connected to the control unit and configured to open responsive to fluid flowing in the first direction; and
   a second one-way valve connected to the control unit and configured to open responsive to fluid flowing in the second direction.

10. The cardiopulmonary bypass device according to claim 1, further comprising a balloon connected to the second tube.

11. The cardiopulmonary bypass device according to claim 10, wherein the balloon is coupled to the control unit.

12. The cardiopulmonary bypass device according to claim 1, further comprising a plurality of sensors coupled to the control unit.

13. The cardiopulmonary bypass device according to claim 12, wherein the sensors are selected from the group of sensors consisting of time sensors, temperature sensors, oxygen level sensors, blood gas sensors, pressure sensors, carbon dioxide and combinations thereof.

14. The cardiopulmonary bypass device according to claim 1, further comprising a ventilation device, for providing lungs with oxygen.

15. The cardiopulmonary bypass device according to claim 14, wherein the ventilation device is a manual ventilation device.

16. The cardiopulmonary bypass device according to claim 14, wherein the ventilation device is an automatic ventilation device coupled to the control unit, the control unit configured to send signal to start and stop the ventilation device.

17. The cardiopulmonary bypass device according to claim 14, wherein the ventilation device comprises a tube for a continuous insufflation of oxygen.

18. The cardiopulmonary bypass device according to claim 1, wherein the control unit further comprises a feedback device for giving feedback to a rescuer.

19. The cardiopulmonary bypass device according to claim 18, wherein the feedback device provides feedback regarding ventilations.

20. The cardiopulmonary bypass device according to claim 1, wherein the control unit comprises a mechanical device configured to control a flow of the fluid out of the pump.

21. The cardiopulmonary bypass device according to claim 1, wherein the control unit comprises an electrical device configured to control a flow of the fluid out of the pump.

22. The cardiopulmonary device according to claim 1, wherein the heat exchange mechanism is configured to cool a first fluid, and wherein the heat exchange mechanism comprises:
a second fluid, cooler than the first fluid, the heat exchange mechanism further configured to thermally couple the second fluid to the first fluid.

23. A cardiopulmonary bypass device comprising:
a first tube configured to connect with at least one vein;
a second tube configured to connect with at least one artery;
a pump coupled to the first and second tubes, the pump being operable in a first mode to pump fluid in a first direction, the pump being further operable in a second mode to pump fluid in a second direction; and
a control unit coupled to the pump and configured to control operation of the pump, the control unit further configured to send a signal to a feedback device for starting and stopping lung ventilation.

24. The cardiopulmonary bypass device according to claim 23, further comprising a heat exchange mechanism configured to cool a fluid.

25. The cardiopulmonary bypass device according to claim 23, further comprising at least one sensor coupled to the control unit.

26. The cardiopulmonary bypass device according to claim 23, further comprising at least one valve coupled to the pump.

27. The cardiopulmonary bypass device according to claim 23, further comprising a fluid reservoir coupled to the pump.

* * * * *